US008118765B2

(12) United States Patent
Magnusson (10) Patent No.: US 8,118,765 B2
(45) Date of Patent: Feb. 21, 2012

(54) JOINT PROTECTOR, BLANK FOR A JOINT PROTECTOR AND METHOD FOR MANUFACTURING A JOINT PROTECTOR

(75) Inventor: Stefan Magnusson, Stockholm (SE)

(73) Assignee: Otto Bock Scandinavia AB, Norrkoping (SE)

( * ) Notice: Subject to any disclaimer, the term of this patent is extended or adjusted under 35 U.S.C. 154(b) by 556 days.

(21) Appl. No.: 11/794,898

(22) PCT Filed: Dec. 30, 2005

(86) PCT No.: PCT/SE2005/002065
§ 371 (c)(1),
(2), (4) Date: Jul. 9, 2007

(87) PCT Pub. No.: WO2006/073353
PCT Pub. Date: Jul. 13, 2006

(65) Prior Publication Data
US 2008/0139982 A1    Jun. 12, 2008

(30) Foreign Application Priority Data
Jan. 7, 2005  (SE) ........................... 0500033

(51) Int. Cl.
*A61F 13/00* (2006.01)

(52) U.S. Cl. ............ 602/63; 602/26; 602/60; 602/61

(58) Field of Classification Search .......... 602/60–64, 602/20, 26, 23; 2/16, 22, 76; 128/856, 892
See application file for complete search history.

(56) References Cited

U.S. PATENT DOCUMENTS

| 663,749 | A | * | 12/1900 | Gorse | 602/60 |
| 4,084,584 | A | | 4/1978 | Detty | |
| 4,474,573 | A | | 10/1984 | Detty | |
| 4,632,106 | A | | 12/1986 | Gamm | 128/165 |
| 5,139,477 | A | * | 8/1992 | Peters | 602/26 |
| 5,154,690 | A | * | 10/1992 | Shiono | 602/5 |
| 5,168,577 | A | | 12/1992 | Detty | 2/16 |
| 5,474,524 | A | | 12/1995 | Carey | |
| 5,603,122 | A | | 2/1997 | Kania | |
| 5,925,010 | A | * | 7/1999 | Caprio, Jr. | 602/62 |
| 6,592,539 | B1 | * | 7/2003 | Einarsson et al. | 602/62 |
| 2001/0007929 | A1 | * | 7/2001 | Schlomski | 602/63 |
| 2003/0083605 | A1 | | 5/2003 | Edmund | |

FOREIGN PATENT DOCUMENTS

| DE | 3519677 A1 | 12/1986 |
| DE | 92 03 328 | 4/1992 |
| WO | WO81/01240 | 5/1981 |

* cited by examiner

*Primary Examiner* — Kim M Lewis
(74) *Attorney, Agent, or Firm* — Jacobson Holman PLLC (57) ABSTRACT

A joint protector of a sheet-shaped flexible material, including an essentially tubular body, which is provided with a curved configuration for adaptation to a joint, and which is sewn together with at least one seam, between a first edge of a first material portion and a second edge of a second material portion, is distinguished in that the seam between said edges extends along a curve, which defines a recessed area of material of the first material portion at an essentially central portion of the first edge, and which defines an enlarged area of material of the second material portion at an essentially central portion of the second edge, that the first material portion is provided with a contracting action to the recessed area of material through the seam for achieving a curved configuration of the tubular body. The invention also concerns a blank and a method.

40 Claims, 4 Drawing Sheets

JOINT PROTECTOR, BLANK FOR A JOINT PROTECTOR AND METHOD FOR MANUFACTURING A JOINT PROTECTOR

This is a national stage of PCT/SE2005/002065 filed 30 Dec. 2005 and published in English.

FIELD OF THE INVENTION

The invention refers to a joint protector, a blank for manufacturing a joint protector and a method for manufacturing a joint protector.

BACKGROUND OF THE INVENTION

From U.S. Pat. No. 4,632,106 is previously known a tube-shaped joint protector of sheet-shaped elastic material adapted to be used on a knee or an elbow. The protector supports the joint to which it is applied and allows movement at the same time as the joint maintains the body temperature so that strain and risks of injuries are limited.

The protector according to the patent document is comprised of a bent, tubular body, which has been provided with the bent configuration by means of transversal seams applied to elongated "eye-shaped" cut-outs in the material.

The previously known device is, however, not flexible enough to provide an adequate curvature of the protector.

AIM AND MOST IMPORTANT FEATURES OF THE INVENTION

It is an aim to provide a joint protector as mentioned above, wherein the problem with the background art is avoided or at least reduced. It is also an aim of the invention to provide a blank as well as a method for manufacturing such a joint protector.

These aims are obtained through features in the following independent patent claims.

By subjecting the recessed area of the material to a contracting effect through the seam, the curved configuration of the body is ensured in a simple and effective way. By providing the recessed area of the material it is also obtained a narrowing of the first material portion in the area of the convex region of the joint protector, which leads to a more even bend with less tendencies of creasing in this area than is the case according to the background art. Further, the joint protector according to the invention is easy to manufacture with a minimum of seams and possibility of avoiding seams in the region of the inside of the joint. It should be noted that in principle "contracting" and "narrowing" means that an even recess having a continuous edge line is effected in this way through it's joining together with an enlargement having a smaller extension and a likewise continuous edge line. It is thus not the question of shortening through seams at edges of removed material, which is the case in U.S. Pat. No. 4,632,106.

It is preferred that also the enlargement area of the material is subjected to a certain deformation in the form of a stretching in connection with sewing together the material portions. This results in a levelling of built-in tensions in the joint protector and a possibility of an even link in the area of the seams.

In particular, the extension of the recessed area of the material exceeds the extension of the enlargement area of the material. In connection with putting together the joint protector there thus occurs a contraction of the recessed area of the material and possibly a stretching of the enlargement area of the material, resulting in the desired curvature.

In particular the desired effect is achieved if the axial height of the first material portion exceeds the axial height of the second material portion. Sewing together results in the above mentioned contraction in a joint state.

By the length of the first edge exceeding the length of the second edge it is achieved during joining together a mutual built-in tension in the length direction of the edges of the joint protector, resulting in that an even material link is experienced between the material portions.

In particular it is preferred that the joint protector has two seams according to the above which may be symmetrically arranged as seen through an axial plane through the joint protector. Nothing, however, excludes that the joint protector is unsymmetrical, that is that the seams on the different sides run differently.

Most preferred is that the first material portion belongs to a first separate piece of material and the second material portion to a second separate piece of material which are joined together through two seams according to the above. It is also preferred that the first material portion is comprised of at least two first, separate pieces of material, for example of different material, colour or with joint effecting properties.

It is preferred that the surface extension of the enlarged area of material is between 40% and 80% of the surface extension of the recessed area of material. Hereby a good adaptation of the bend is achieved, which is excellent in most applications. It should be noted that also other proportions may prevail.

It is preferred also that the enlarged area of material has a general tapering angle which is about 10°-45° less than a general tapering angle of the recessed area of material. This is a way of expressing that the enlarged area of the material extends with a curve which is more acute or more pointed than the curve of the edge of the recessed area of the material. When joining together, the recessed area of the material will hereby be contracted against said more acute or more pointed curve.

By the shortest distance between the bottoms of two recessed areas of material of the respective seam being between 10% and 40% of the length of the circumference of the joint protector, an advantageous combination of curvature, crease-freedom and produceability is achieved.

It is preferred that the joint protector according to the invention is made from a laminate of a stretch textile material, for example knitted textile material, on each side of a porous layer of rubber or a rubber-like material, for example neoprene rubber having enclosed gas pores. Also other materials can, however, be used such as for example a distance tricot or common knitted or woven materials. For the sake of elasticity in these materials, there are preferably provided elastic threads of for example rubber or rubber-like material (for example Elasthane™).

The joint protector according to the invention can be produced having different portions of different materials with different properties and also be provided with a shock receiving protective portion, which is advantageous in application for example in sports protectors.

Corresponding advantages are achieved through the other independent and dependent claims.

BRIEF DESCRIPTION OF DRAWINGS

The invention will now be described in greater detail by way of embodiments and with reference to the annexed drawings, wherein.

DESCRIPTION OF EMBODIMENTS

In the following description similar and like details are indicated with the same reference numerals.

Figure 1:
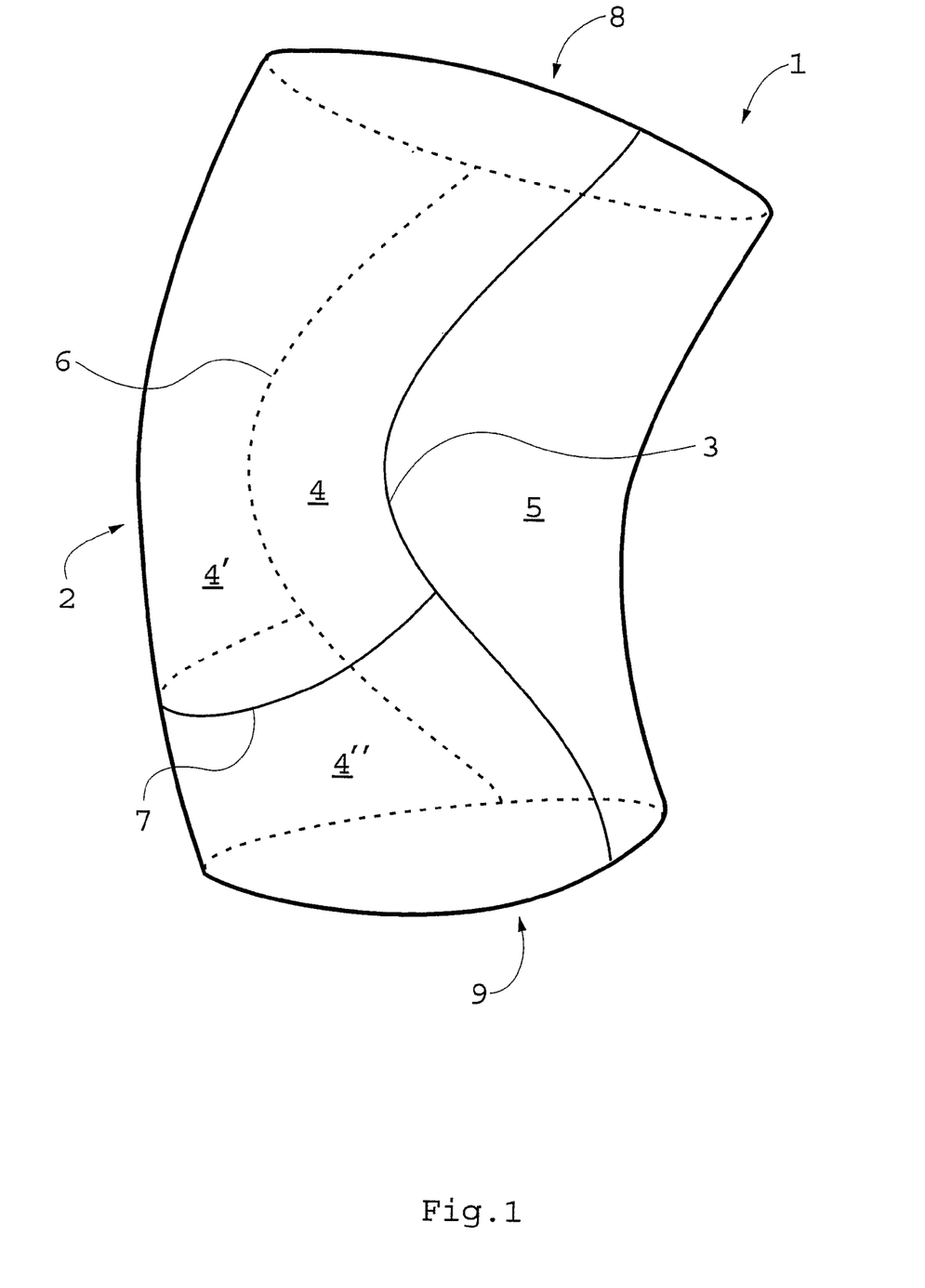
FIG. 1 shows a joint protector according to the invention according to a first embodiment.

In FIG. 1 reference numeral 1 concerns a joint protector in the form of a knee protector for performing sports in the form of a bent, tubular body made from a suitable flexible material such as preferably a layer of porous neoprene rubber laminated on each side with knitted textile material, or any other material which per se is previously known with respect to protectors of this kind.

Because of its curvature, the joint protector 1 has a convex region 2 to be comfortably adapted to the extreme portion of the joint, in this case the knee cap. The joint protector according to the invention can also be used for other joints such as elbows.

The joint protector 1 has a seam extending essentially longitudinally between the first material portion 4 and the second material portion 5. The seam 3 between these material portions extends along a curve in a manner which is to be explained below, and which is made so that the first material portion 4 is subjected to a contracting action for achieving the curved configuration of the tubular body. In the joint protector 1 in FIG. 1, the first material portion 4 belongs to a first material piece and the second material portion 5 to a second material piece. For this purpose the joint protector also has a second seam 6, which is marked with an interrupted line essentially longitudinally to the joint protector, essentially on the opposite side to the seam 3. The seams 3 and 6 thus co-operate in order to achieve the curved configuration of the joint protector. The "longitudinal direction" or "axial direction" of the joint protector 1 is defined as the direction between an upper opening at reference numeral 8 and a lower opening at reference numeral 9.

In the joint protector 1 in FIG. 1, the first material piece which includes the first material portion 4 has two parts, 4' and 4", which are joined together by means of a further essentially transversal seam 7. Such a separation could be arranged for aesthetic reasons or for practical reasons, whereby in that case the parts 4' and 4" can be made from different materials having different properties for different parts of the protector. In its simplest form, the joint protector is made without this seam 7 and the material piece including the portion 4 consists of one single piece of material.

An important aspect of a joint protector according to the invention is to make it slightly narrowing in its central portion that is having a slight "hour-glass shape". This gives good adjustment to the joint and the widened shape of the adjacent portions of arms and legs, so that a joint protector is prevented from sliding from its correct position when the joint articulates. The inventive joint protector gives good possibilities of achieving a gently adapted curvature of the joint protector in order to achieve such a central narrowing without creasing and irregularities.

Figure 2:
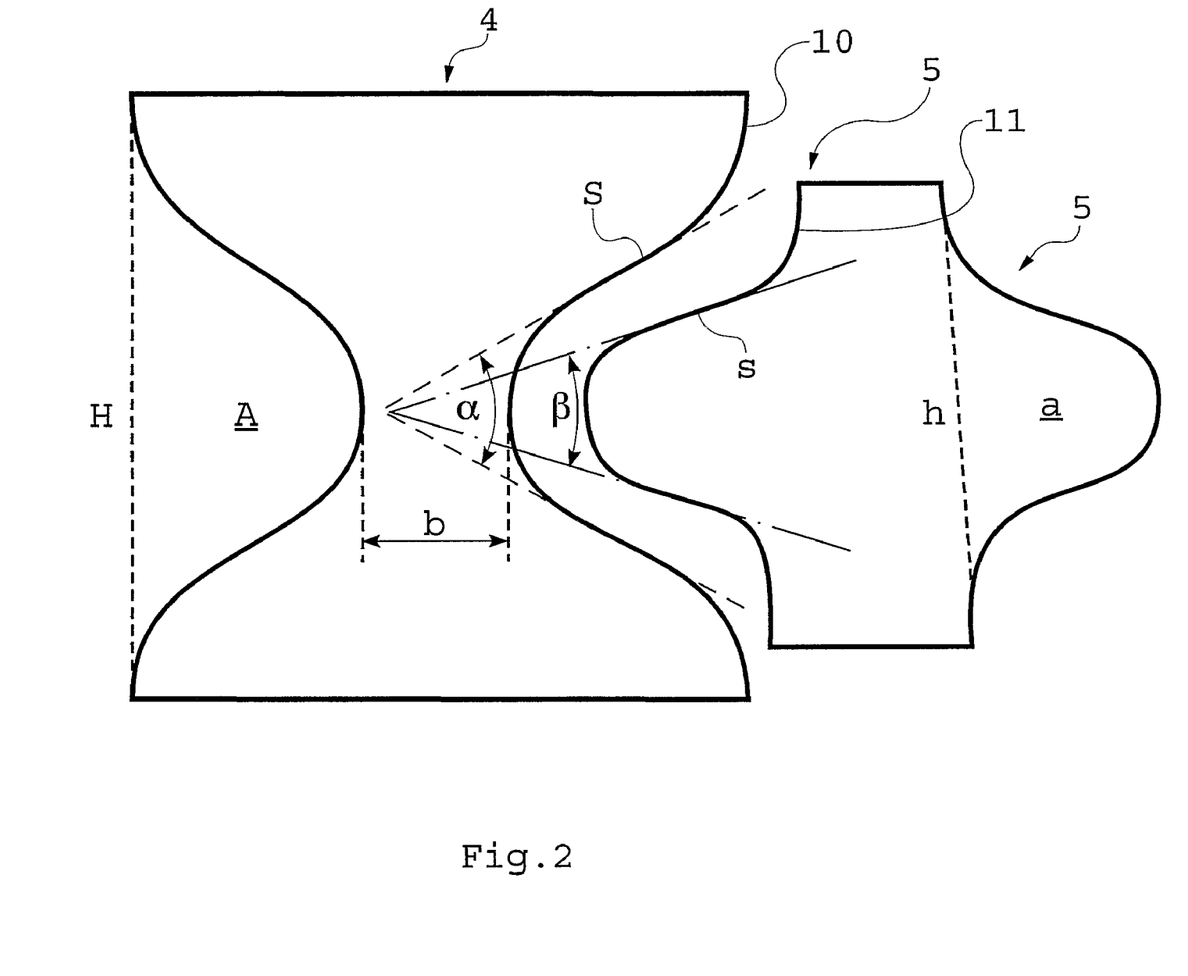
FIG. 2 shows a blank consisting of two blank parts to be joined together into a joint protector according to the invention.

In FIG. 2 a blank of a joint protector according to the invention is shown including two pieces of material, a first piece of material including said first material portion 4 and a second piece of material including said second material portion 5. For joining together these parts into a joint protector, the parts are sewn together with a seam essentially longitudinally of the completed joint protector between a first edge 10 of the first material portion 4 and a second edge 11 of the second material portion 5.

As is shown in FIG. 2, the first edge 10 extends along a first curve defining a recessed area of material along an essentially central portion of its extension, said recessed area of material being indicated with A on the left part of the, in this case, symmetrical piece of material.

The second edge 11 extends along a second curve which defines an enlarged area of material, a, along an essentially central part of its extension, said enlarged area of material being limited at the right part of this piece of material with an interrupted line.

As is shown in the figure the enlarged area of the material, a, has a general tapering angle D which is smaller than a general tapering angle a of the recessed area of material. The curve S is thus shallower than the curve s. It is preferred that P is about 10°-45° smaller than α.

The surface extension of the enlarged area of material, a, is also smaller than the surface extension of the recessed area of material, A. It is preferred that the surface extension of the enlarged area of material is between 40% and 80% of the surface extension of the recessed area of material.

s is also shorter than S. The height h of the second piece of material is also smaller than the height H of the first piece of material. Altogether these parameters for forming the different portions result in that a joining together of the first edge 10 with the second edge 11 will result in a contracting action to the recessed area of material, with or without tension provided between the two portions, so that the completed protector will receive the desired curved configuration. It is thus possible to join together the protector in such a way that the edges 10 and 11 are essentially equally long and that thus no tensile tension exists between the different parts. It is, however, preferred that the second edge 11 in an unloaded state is shorter than the first edge 10 in an unloaded state, whereby, when joining by sewing, the shorter edge is subjected to a certain stretching and the resulting seam distributes sideward tension between the material portions that are sewn together. This results in a good link between the material portions and contributes to providing the joint protector with desired properties. Preferably the blank parts are subjected to different degrees of stretching and/or possibly contraction along different portions of their extension, for example a higher degree of stretching on non-central parts of the material portion which is subjected to the stretching. This can easily be marked by providing edges to be sewn together with indexing points which are intended to coincide in connection with the sewing.

It should be observed that with "blank" in this case also is intended blanks being comprised of a plurality, e.g. two, pieces of material.

Figure 3:
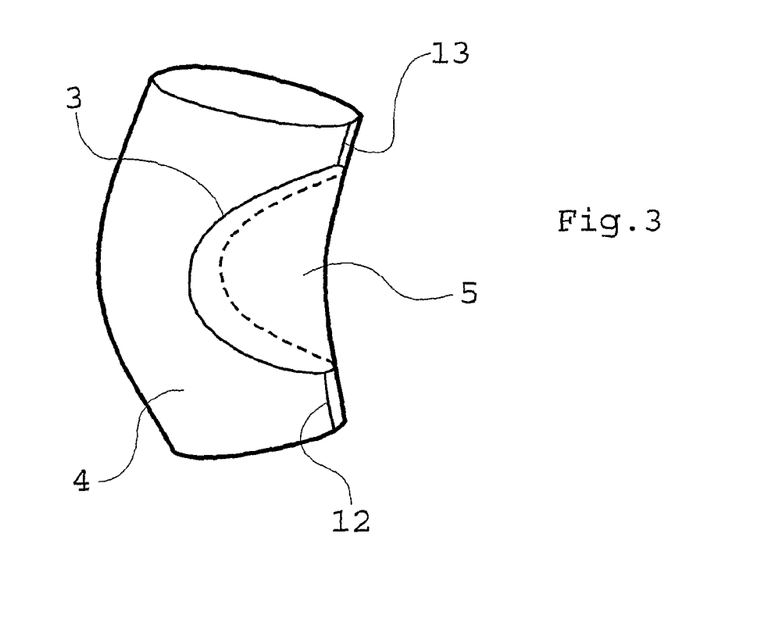
FIG. 3 shows diagrammatically a joint protector according to a second embodiment of the invention.

In FIG. 3 there is diagrammatically shown a joint protector, wherein a first piece of material 4 completely encloses a second piece of material 5, wherein the edges sewn together by a seam 3 of said material portions 4 and 5 are shaped according to what is described above in connection with FIGS. 1 and 2. In this case, however, the material portion 5 with its corresponding piece of material is completely enclosed by the piece of material of the material portion 4. The reference numerals 12 and 13 concern seams for providing the piece of material including the material portion 4 a tubular form. In this case the seam 3 is said contracting seam. Also this can be defined to have at least portions which extend longitudinally of the joint protector.

As an alternative a joint protector can of course be contemplated, wherein a material portion 5 is enclosed at one end of the joint protector, for example at the upper one, but at the lower end of the joint protector extends according to what is shown in FIG. 1.

Figure 4:
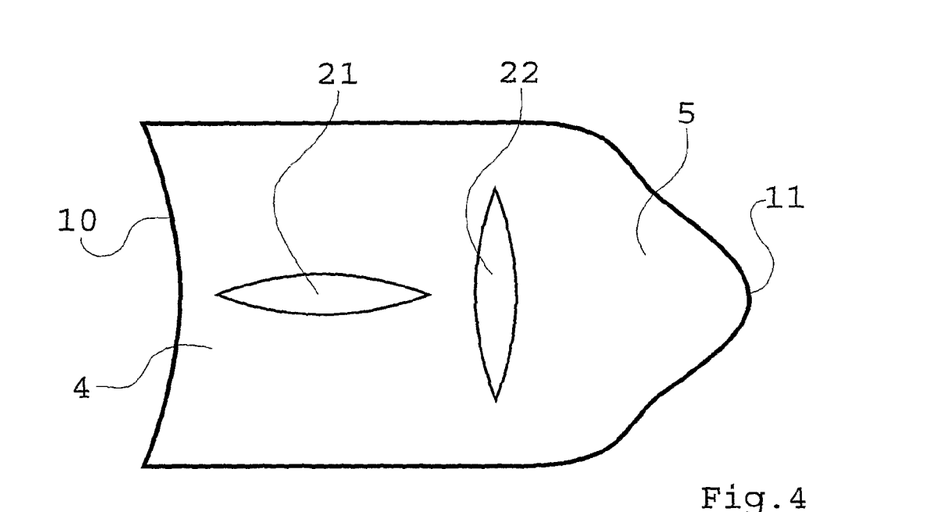
FIG. 4 shows diagrammatically a blank according to a further embodiment of the invention.

In FIG. 4 is shown an integral blank in one single piece which includes the first material portion 4 as well as the second material portion 5. In this case it could be appropriate to provide cut-outs along the extension of the blank, such as a transversal cut-out 21 and a longitudinal cut-out 22 as seen in the "axial" direction of the completed joint protector, which are sewed together in order to provide a middle portion of the blank in FIG. 4 with the desired properties. Other shapes and positions of these cut-outs can be envisaged.

Figure 5:
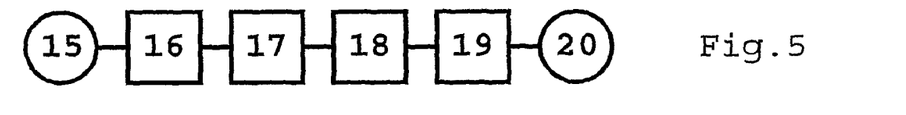
FIG. 5 shows diagrammatically a sequence concerning a method according to the invention.

In FIG. 5 is diagrammatically shown a sequence concerning a method for producing a joint protector according to the invention, wherein position 15 indicates the start of the sequence.

Position 16 concerns providing a first material portion formed with a recessed area of material of an essentially central part of the first edge.

Position 17 concern providing a second material portion shaped with an enlarged area of material at an essentially central part of the second edge.

Position 18 indicates bringing together the edges and possibly stretching the edge of the second material portion.

Position 19 concerns sewing together the edges of the material portions, wherein the first material portion is subjected to a contracting action of the recessed area of material in order to obtain the curved configuration of a resulting tubular body.

Position 20 indicates the end of the sequence.

Figure 6:
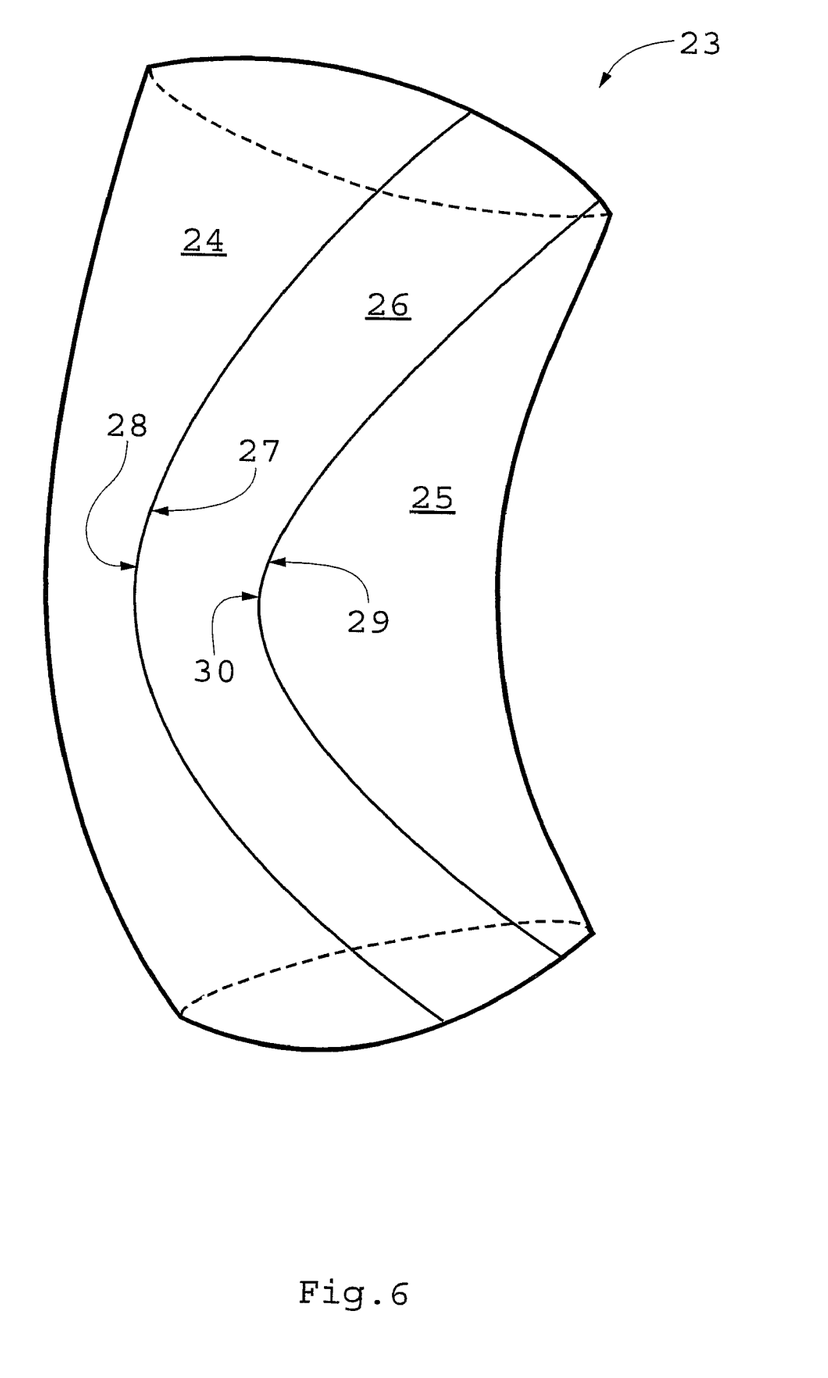
FIG. 6 shows a joint protector of the invention according to a further embodiment.

FIG. 6 shows a joint protector according to a second embodiment, wherein a first material portion 24 has a recessed area of material 27 which is sewn together with an enlarged area of material 28 of a second material portion 26. Further this second material portion 26 has a recessed area of material 29, which is sewn together with an enlarged area of material 30 of a third material portion 25. Both seams of the edges 27, 28 and 29, 30, respectively, are performed at enlarged areas of material/recessed area of material, which are formed as is described above in order in both cases that the material portions are to be provided with a contracting action through the seams of the recessed areas of material.

It is also possible to have a fourth material portion sewn between the first and the third material portions and providing an enlarged area of material sewn together with a recessed area of material of the first material portion and a recessed area of material sewn together with an enlarged area of material of the third material portion, wherein all recessed areas of material are provided with a contracting action by the seams.

Through this embodiment, which is described in connection with FIG. 6, it is achieved a more distributed contracting effect of the material pieces, whereby this effect can be said to occur in two steps on each side of the protector where it is applied. For each step the differences may be made smaller between the meeting edges and still a considerable total effect be obtained.

The invention can be modified further within the scope of the annexed claims. Thus, the shapes of the protectors as well as the materials of the different portions may be varied. The joint protector can thus include portions of non-elastic (but flexible) properties. It is not excluded that further seams or recesses can be supplied on different parts of the joint protector, for example from aesthetic or practical reasons.

For best effect, the joint protector according to the invention should include material having a stretching ability exceeding about 25% and preferably over 30% and also up to and exceeding 100%. This makes it possible to have good adaption to the desired form and that further stretching resources remain in order to make it possible for a joint which is received by the joint protector to be optimally bent.

The invention claimed is:

1. A joint protector of a sheet-shaped flexible material, including an essentially tubular body, which is provided with a curved configuration for adaptation to a joint, so that the joint protector defines a convex area for adaptation to an extreme portion of the joint, and which is sewn together with at least one seam, essentially longitudinally of the protector, between a first edge of a first material portion and a second edge of a second material portion, said joint protector comprising the seam between said edges extending along a curve, which defines a recessed area of material of the first material portion at an essentially central portion of the first edge, and which defines an enlarged area of material of the second material portion at an essentially central portion of the second edge, the first material portion being provided with a contracting action to the recessed area of material through the seam for achieving a curved configuration of the tubular body by an extension of the recessed area of material exceeding an extension of the enlarged area of material in an unloaded condition, and a length of the first edge exceeding a length of the second edge in the unloaded condition, the first material portion belonging to at least two first pieces of material.

2. The joint protector according to claim 1, wherein the second material portion is provided with a stretching effect to the enlarged area of material.

3. The joint protector according to claim 1, wherein the axial height of the first material portion exceeds the axial height of the second material portion in an unloaded condition as seen in the axial direction of the joint protector.

4. The joint protector according to claim 1, further comprising two seams at essentially opposite sides in order to achieve the curved configuration of the tubular body.

5. The joint protector according to claim 1, wherein the first material portion belongs to a first piece of material and that the second material portion belongs to a second piece of material.

6. The joint protector according to claim 1, wherein in an unloaded state the surface extension of the enlarged area of material is between about 40% and 80% of the surface extension of the recessed area of material.

7. The joint protector according to claim 1, wherein in an unloaded state, the enlarged area of material has a general tapering angle, which is about 10°-45° smaller than a general tapering angle of the recessed area of material.

8. The joint protector according to claim 1, wherein the shortest distance between the bottoms of two recessed areas of material of the respective seam is between about 10% and 40% of the length of the circumference of the joint protector.

9. The joint protector according to claim 1, wherein the sheet-shaped flexible material is comprised of a laminate of a layer of stretch material such as knitted textile material on each side of a porous layer of rubber or rubber-like material.

10. The joint protector according to claim 1, further comprising a shock absorbing protective portion.

11. The joint protector according to claim 10, wherein the shock absorbing protective portion is sewn with said seam or seams.

12. The joint protector according to claim 1, wherein said seam or seams at least partially extend essentially longitudinally of the joint protector.

13. The joint protector according to claim 1, wherein a further edge of the second material portion, opposite to said second edge is sewn to an edge of a third material portion, wherein the seam between these edges extends along a curve which defines a second recessed area of material of the second material portion at an essentially central portion of the additional edge, and which defines a second enlargement of material of the third material portion at an essentially central portion of the edge of this material portion, wherein the second material portion is provided with a contracting action of the second recessed area of material by the seam.

14. The joint protector according to claim 13, wherein a fourth material portion is sewn between the first and the third material portion and has an enlarged area of material sewn together with a recessed area of material of the first material portion and a recessed area of material sewn together with an enlarged area of material of the third material portion, wherein all recessed areas of material are provided with a contracting action through the seams.

15. A blank of a sheet-shaped flexible material for a joint protector which includes an essentially tubular body which is provided with a curved configuration for adaptation to a joint, so that the protector defines a convex area for adaptation to an extreme portion of the joint, and wherein said blank is intended to be sewn together to said tubular body with at least one seam essentially longitudinally of the protector between a first edge of a first material portion of said blank and a second edge of a second material portion of said blank, said blank comprising
the first edge extending along a first curve which defines a recessed area of material along an essentially central part of its extension,
the second edge extending along a second curve which defines an enlarged area of material along an essentially central part of its extension, and
the extension of the recessed area of material exceeding the extension of the enlarged area of material to achieve a curved configuration of the tubular body in a state where it is joined together, the length of the first edge exceeding the length of the second edge.

16. The blank according to claim 15, wherein the axial height of the first material portion exceeds the axial height of the second material portion as seen in the axial direction of the completed joint protector.

17. The blank according to claim 15, wherein the first material portion belongs to a first piece of material and the second material portion belongs to a second piece of material.

18. The blank according to claim 15, wherein the first material portion belongs to at least two first pieces of material.

19. The blank according to claim 15, wherein the surface extension of the enlarged area of material is between about 40% and 80% of the surface extension of the recessed area of material.

20. The blank according to claim 15, wherein the enlarged area of material has a general tapering angle which is about 10°-45° smaller than a general tapering angle of the recessed area of material.

21. The blank according to claim 15, wherein the shortest distance between the bottoms of two recessed areas of material of the respective seam is about 10% and 40% of the length of the circumference of the completed joint protector.

22. The blank according to claim 15, wherein the sheet-shaped flexible material is comprised of a laminate of a layer of stretch material such as knitted textile material on each side of a porous layer of rubber or a rubber-like material.

23. The blank according to claim 15, wherein
a further edge of the second material portion, opposite to said second edge, defines a second recessed area of material at an essentially central portion of the further edge,
and a third material portion defines a second enlarged area of material at an essentially central portion of the edge of this material portion, wherein the extension of the second recessed area of material exceeds the extension of the second enlarged area of the material in order to obtain the curved configuration of the tubular body in its completed state.

24. The blank according to claim 23, further comprising
a fourth material portion for sewing together between the first and the third material portion which has an enlarged area of material for co-operation with a recessed area of material of the first material portion and a recessed area of material for co-operation with an enlarged area of material of the third material portion, for obtaining a contracting action through the seams of all recessed areas of material.

25. A method for manufacturing a joint protector of a sheet-shaped flexible material, including an essentially tubular body, which is provided with a curved configuration for adaptation to a joint, so that the joint protector defines a convex area for the adaption to an extreme portion of the joint, including the step: sewing together with at least one seam, essentially longitudinally of the protector, a first edge of a first material portion with a second edge of a second material portion, said method comprising the steps of
providing the first material portion with a recessed area of material at an essentially central portion of the first edge,
providing the second material portion with an enlarged area of material at an essentially central portion of the second edge, and
providing the first material portion of a contracting action to the recessed area material by the seam in order to achieve the curved configuration of the tubular body an extension of the recessed area of material exceeding an extension of the enlarged area of material in an unloaded condition, a length of the first edge exceeding a length of the second edge in the unloaded condition, and the first material portion belonging to at least two first pieces of material.

26. The method according to claim 25, further comprising providing the second material portion with a stretching action to the enlarged area of material.

27. The method according to claim 25, further comprising forming the first material portion with an axial height which exceeds the axial height of the second material portion as seen in the axial direction of the joint protector.

28. The method according to claim 25, wherein two seams are performed essentially longitudinal of the joint protector, on essentially opposite sides, in order to obtain the curved configuration of the tubular body.

29. The method according to claim 25, further comprising providing a first piece of material including the first material portion and a second piece of material including the second material portion.

30. The method according to claim 25, further comprising providing the enlarged area of material with a surface extension of between 40% and 80% of the surface extension of the recessed area of material.

31. The method according to claim 25, further comprising providing the enlarged area of material with a general tapering angle, which is about 10°-45° smaller than a general tapering angle of the recessed area of material.

32. The method according to claim 25, further comprising forming the first piece of material such that the shortest distance between the bottoms of two recessed areas of material of the respective seam is between about 10% and 40% of the length of the circumference of the joint protector.

33. The method according to claim 25, wherein the sheet-shaped flexible material is comprised of a laminate of stretch material such as knitted textile material on each side of a porous layer of rubber or rubber-like material.

34. The method according to claim 25, wherein said seam or seams at least partially extend essentially longitudinally of the joint protector.

35. The method according to claim 25, further comprising providing a third material portion for insertion between the first and the second material portion and possibly a fourth material portion for insertion between the first and the third material portion.

36. A joint protector of a sheet-shaped flexible material, including an essentially tubular body, which is provided with a curved configuration for adaptation to a joint, so that the joint protector defines a convex area for adaptation to an extreme portion of the joint, and which is sewn together with at least one seam, essentially longitudinally of the protector, between a first edge of a first material portion and a second edge of a second material portion, said joint protector comprising the seam between said edges extending along a curve, which defines a recessed area of material of the first material portion at an essentially central portion of the first edge, and which defines an enlarged area of material of the second material portion at an essentially central portion of the second edge, the first material portion being provided with a contracting action to the recessed area of material through the seam for achieving a curved configuration of the tubular body by an extension of the recessed area of material exceeding an extension of the enlarged area of material in an unloaded condition, and a length of the first edge exceeding a length of the second edge in the unloaded condition, the surface extension of the enlarged area of material, in an unloaded state, being between about 40% and 80% of the surface extension of the recessed area of material.

37. A joint protector of a sheet-shaped flexible material, including an essentially tubular body, which is provided with a curved configuration for adaptation to a joint, so that the joint protector defines a convex area for adaptation to an extreme portion of the joint, and which is sewn together with at least one seam, essentially longitudinally of the protector, between a first edge of a first material portion and a second edge of a second material portion, said joint protector comprising the seam between said edges extending along a curve, which defines a recessed area of material of the first material portion at an essentially central portion of the first edge, and which defines an enlarged area of material of the second material portion at an essentially central portion of the second edge, the first material portion being provided with a contracting action to the recessed area of material through the seam for achieving a curved configuration of the tubular body by an extension of the recessed area of material exceeding an extension of the enlarged area of material in an unloaded condition, and a length of the first edge exceeding a length of the second edge in the unloaded condition, the enlarged area of material having a general tapering angle, in an unloaded state, which is about 10°-45° smaller than a general tapering angle of the recessed area of material.

38. A joint protector of a sheet-shaped flexible material, including an essentially tubular body, which is provided with a curved configuration for adaptation to a joint, so that the joint protector defines a convex area for adaptation to an extreme portion of the joint, and which is sewn together with at least one seam, essentially longitudinally of the protector, between a first edge of a first material portion and a second edge of a second material portion, said joint protector comprising the seam between said edges extending along a curve, which defines a recessed area of material of the first material portion at an essentially central portion of the first edge, and which defines an enlarged area of material of the second material portion at an essentially central portion of the second edge, the first material portion being provided with a contracting action to the recessed area of material through the seam for achieving a curved configuration of the tubular body by an extension of the recessed area of material exceeding an extension of the enlarged area of material in an unloaded condition, and a length of the first edge exceeding a length of the second edge in the unloaded condition, the shortest distance between the bottoms of two recessed areas of material of the respective seam being between about 10% and 40% of the length of the circumference of the joint protector.

39. A joint protector of a sheet-shaped flexible material, including an essentially tubular body, which is provided with a curved configuration for adaptation to a joint, so that the joint protector defines a convex area for adaptation to an extreme portion of the joint, and which is sewn together with at least one seam, essentially longitudinally of the protector, between a first edge of a first material portion and a second edge of a second material portion, said joint protector comprising the seam between said edges extending along a curve, which defines a recessed area of material of the first material portion at an essentially central portion of the first edge, and which defines an enlarged area of material of the second material portion at an essentially central portion of the second edge, the first material portion being provided with a contracting action to the recessed area of material through the seam for achieving a curved configuration of the tubular body by an extension of the recessed area of material exceeding an extension of the enlarged area of material in an unloaded condition, and a length of the first edge exceeding a length of the second edge in the unloaded condition, a further edge of the second material portion, opposite to said second edge being sewn to an edge of a third material portion, the seam between these edges extending along a curve which defines a second recessed area of material of the second material portion at an essentially central portion of the additional edge, and which defines a second enlargement of material of the third material portion at an essentially central portion of the edge of this material portion, the second material portion being provided with a contracting action of the second recessed area of material by the seam.

40. The joint protector according to claim 39, wherein a fourth material portion is sewn between the first and the third material portion and has an enlarged area of material sewn together with a recessed area of material of the first material portion and a recessed area of material sewn together with an enlarged area of material of the third material portion, wherein all recessed areas of material are provided with a contracting action through the seams.

* * * * *